US012797355B2

(12) United States Patent
Yuan et al.

(10) Patent No.: US 12,797,355 B2
(45) Date of Patent: Nov. 17, 2026

(54) USE OF SULFORAPHENE IN PREPARATION OF PHARMACEUTICAL COMPOSITION FOR IMPROVING AND TREATING LEUKOTRICHIA AND/OR ALOPECIA

(71) Applicant: Beijing University of Chemical Technology, Beijing (CN)

(72) Inventors: Qipeng Yuan, Beijing (CN); Pengtao Liu, Beijing (CN); Li Cheng, Beijing (CN)

(73) Assignee: Beijing University of Chemical Technology, Beijing (CN)

( * ) Notice: Subject to any disclaimer, the term of this patent is extended or adjusted under 35 U.S.C. 154(b) by 454 days.

(21) Appl. No.: 18/288,795

(22) PCT Filed: Sep. 8, 2022

(86) PCT No.: PCT/CN2022/117853
§ 371 (c)(1),
(2) Date: Oct. 27, 2023

(87) PCT Pub. No.: WO2023/061117
PCT Pub. Date: Apr. 20, 2023

(65) Prior Publication Data

US 2024/0216324 A1 Jul. 4, 2024

(30) Foreign Application Priority Data

Oct. 15, 2021 (CN) ......................... 202111203285.5

(51) Int. Cl.
*A61K 36/31* (2006.01)
*A61K 31/26* (2006.01)
*A61P 17/14* (2006.01)

(52) U.S. Cl.
CPC .............. *A61K 31/26* (2013.01); *A61K 36/31* (2013.01); *A61P 17/14* (2018.01); *A61K 2236/15* (2013.01); *A61K 2236/39* (2013.01)

(58) Field of Classification Search
None
See application file for complete search history.

(56) References Cited

U.S. PATENT DOCUMENTS

2008/0027129 A1* 1/2008 Commo ............... A61K 8/4986 514/441

OTHER PUBLICATIONS

Sangthong et al. (2016) Food Chemistry 201: 139-144. (Year: 2016).*
Sham et al. (2013) Evidence-Based Complementary and Alternative Medicine vol. 2013 Article 636194 (16 pages) (Year: 2013).*
Subedi et al. (2025) J. Mol. Sci. 26: 7467 (33 pages). (Year: 2025).*

* cited by examiner

*Primary Examiner* — Russell G Fiebig
(74) *Attorney, Agent, or Firm* — Robert C. Klinger; CM Law LLP

(57) ABSTRACT

The present disclosure provides use of sulforaphene in preparation of a pharmaceutical composition for improving and treating leukotrichia and/or alopecia, and a preparation method of the pharmaceutical composition. The sulforaphene serves as an active ingredient of the pharmaceutical composition, and the sulforaphene has a content of 0.1% to 50% based on a total weight of the pharmaceutical composition.

19 Claims, 2 Drawing Sheets

Figure 1:
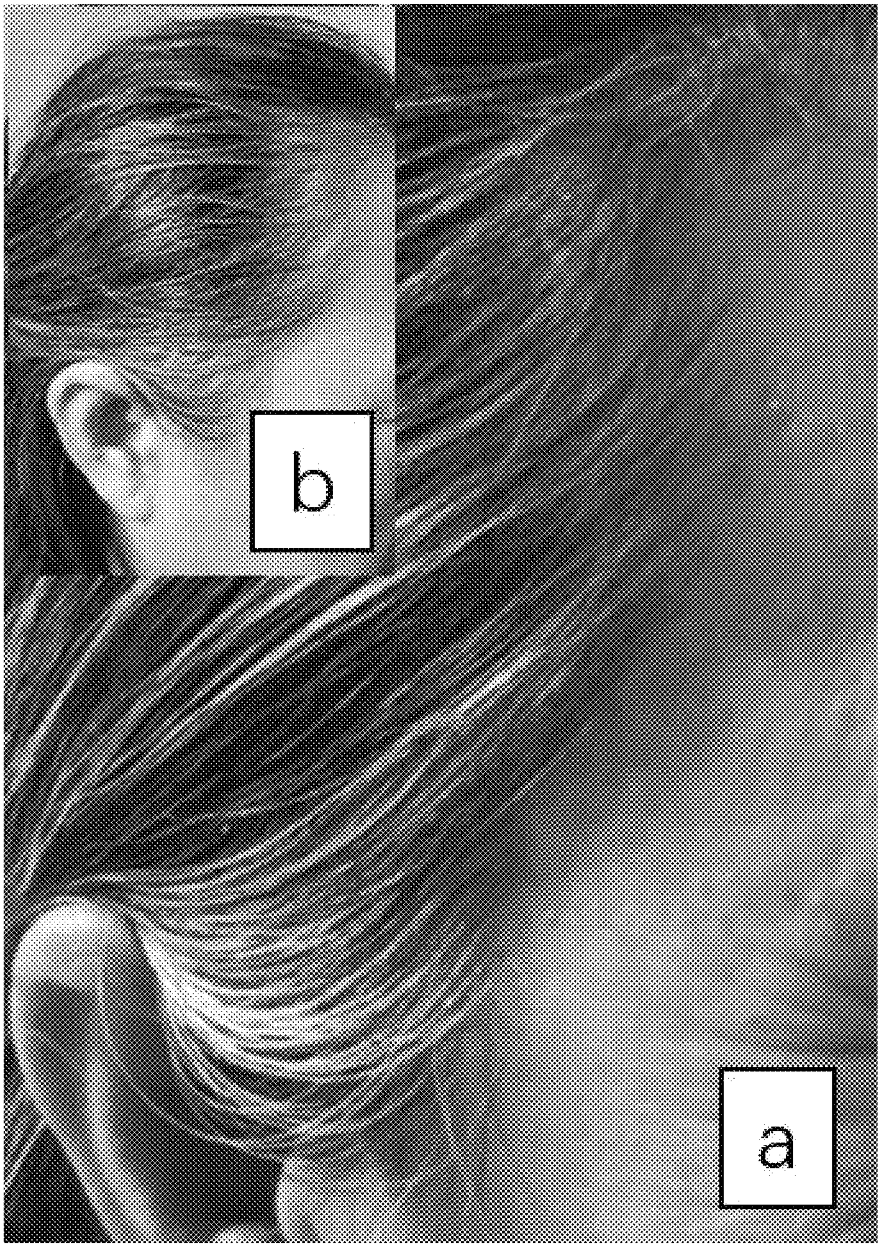

USE OF SULFORAPHENE IN PREPARATION OF PHARMACEUTICAL COMPOSITION FOR IMPROVING AND TREATING LEUKOTRICHIA AND/OR ALOPECIA

CROSS-REFERENCE TO RELATED APPLICATION

This patent application is a national stage application of International Patent Application No. PCT/CN2022/117853, filed on Sep. 8, 2022, which claims the benefit and priority of Chinese Patent Application No. 202111203285.5, filed with the China National Intellectual Property Administration on Oct. 15, 2021, the disclosure of which is incorporated by reference herein in its entirety as part of the present application.

TECHNICAL FIELD

The present disclosure relates to use of sulforaphene in preparation of a pharmaceutical composition for improving and treating leukotrichia and/or alopecia, where the sulforaphene serves as an active ingredient of the pharmaceutical composition. The present disclosure further relates to a preparation method of the pharmaceutical composition.

BACKGROUND

Leukotrichia can be divided into congenital leukotrichia and acquired leukotrichia. The congenital leukotrichia generally shows a family history, and the acquired leukotrichia includes senile leukotrichia and juvenile leukotrichia. The senile leukotrichia is related to old age and frailty, while the juvenile leukotrichia is related to nutritional disorders or mental factors. Some chronic disease factors may also cause the leukotrichia. The leukotrichia can also be divided into physiological leukotrichia and pathological leukotrichia. The physiological leukotrichia is the senile leukotrichia, and the pathological leukotrichia can be divided into nutritional metabolism-caused leukotrichia, chemical leukotrichia, and hereditary leukotrichia.

Researches in Non-Patent Document 1 suggest that leukotrichia is caused by a weakened melanin-producing function of melanocytes and a decrease in tyrosinase activity. Deletion of a β-lymphocytoma-2 gene (bcl-2) induces apoptosis in melanocyte stem cells and weakens specialized enzymatic antioxidant defense systems. This mechanism exacerbates oxidative stress processes, such as a reduction in catalase, which leads to accumulation of hydrogen peroxide that disables and kills globular melanocytes. Microphthalmia-associated transcription factor (MITF) has a transcriptional regulatory effect on the tyrosinase-related protein family and is involved in melanin production.

Alopecia is divided into normal physiological alopecia and pathological alopecia. The normal physiological alopecia can keep the hair entering a catagen phase and the hair newly entering a growth phase in a constant dynamic balance, such that the normal number of hair can be maintained. However, the pathological alopecia causes abnormal or excessive hair loss. There are complex causes of the pathological alopecia, and the pathological alopecia includes, for example, androgenetic alopecia, neuropathic alopecia, endocrine alopecia, nutritional alopecia, and congenital alopecia.

Patent Document 1 describes the alopecia caused by disorders of androgen metabolism. Specifically, an enhanced activity of 5α-reductase causes excessive conversion of testosterone into dihydrotestosterone. The dihydrotestosterone accumulates in large amounts among the scalp hair follicles, resulting in shortened hair growth cycles, hair follicle degeneration and shrinkage, as well as hair thinning, softening, shortening, and falling off.

At present, control methods for the leukotrichia and alopecia include traditional Chinese medicine therapy and Western medicine therapy. In Patent Document 2, traditional Chinese medicine believes that the following factors are related to leukotrichia: one is the deficiency of essence and blood: the deficiency of kidney essence cannot metabolize and produce Yin blood, and the deficiency of Yin blood causes the hair to lose nourishment, thus turning white gray. The second is excessive blood heat: emotional excitement causes the kidney failing to nourish liver, such that the liver-fire is strong and the blood is dry, and the excessive blood heat leads to the loss of nourishment of the hair roots, so the hair turns white prematurely. The third is liver stagnation and spleen dampness: the stagnation of liver qi causes damage to the heart and spleen, the damages of spleen lead to negligence of transportation and transformation, such that there is no source of qi and blood generation, and the hair becomes white.

Patent Document 3 disclosed a capsule for treating juvenile leukotrichia, including traditional Chinese medicines *Fructus Ligustri Lucidi, Herba Ecliptae*, Mulberry Fruit, *Radix Glycyrrhizae*, black sesame, and gelatin, where the capsule is processed through a technological process of capsule products. Patent Document 4 disclosed a traditional Chinese medicine composition and a granule thereof for blackening hair, including *Fructus Ligustri Lucidi, Herba Ecliptae, Radix polygoni Multiflori Praeparata, Rhizoma Polygonati*, and black soybean, where the granule is processed through a technological process of granular pharmaceutical products. None of these traditional Chinese medicine therapies has found any component that shows a significant effect in controlling leukotrichia, while side effects caused by multiple components cannot be ignored and are also a common shortcoming of the traditional Chinese medicine therapies.

Regarding Western medicine therapy, Patent Document 5 disclosed a composition and a method for controlling or slowing down hair discoloration. The composition includes a catalase, an anti-oxidant, and a cosmetic product carrier, and has a pH value controlled at 2 to 6. A substance containing the composition acts directly on mid-section to root of the hair to control or slow down graying of the hair. However, an influence of the composition described in this document on melanocytes and tyrosinase has not been thoroughly studied, there is also a poor effect on preventing black hair from graying, and this composition may have potential side effects.

Non-patent Document 2 discloses that sulforaphene is an isothiocyanate capable of being extracted from natural products such as *Semen raphani* and radish seeds. At present, the research on sulforaphene mainly focuses on its anti-cancer functions. This substance can efficiently induce phase-II detoxification enzymes to improve the human body's capacity to scavenge carcinogens. Therefore, the sulforaphene can effectively inhibit the growth and proliferation of cancer cells and kill cancer cells. The research in Non-Patent Document 3 also shows that the sulforaphene shows a desirable killing effect on cancer cell lines such as lung cancer and liver cancer, and can also inhibit esophageal cancer and breast cancer cells.

However, the application of sulforaphene in improving and treating leukotrichia and/or alopecia has not been reported so far.

DOCUMENTS IN THE PRIOR ART

Patent Document 1: CN108066221A
Patent Document 2: CN105660933A
Patent Document 3: CN104415101A
Patent Document 4: CN104606485A
Patent Document 5: U.S. Pat. No. 9,265,717B1
Non-Patent Document 1: Transcriptional regulation of tyrosinase-related proteins by MITF in normal human melanocytes, *J Med Res*, March 2013, Vol 42 No. 3. 58-62
Non-Patent Document 2: Yang, M., Ren, M., Qu, Y., Teng, W., Wang, Z., Li, H. and Yuan, Q., 2016. Sulforaphene inhibits hepatocellular carcinoma through repressing keratin 8 and activating anoikis. *RSC Advances,* 6(74), pp. 70326-70334
Non-Patent Document 3: Evaluation of antitumor activity and research of mechanism of action on a plant-derived natural compound sulforaphene, Yue Qu, master's thesis of Beijing University of Chemical Technology, 2015, abstract

SUMMARY

Technical Problem to be Solved by the Present Disclosure

It can be seen from the background that leukotrichia and alopecia occur for many reasons, and bring adverse effects to people both in appearance and in spirit. However, traditional Chinese medicine and Western medicine therapies have various defects and deficiencies currently. Traditional Chinese medicine therapy has slow efficacy and long-term side effects caused by multi-components, and some of which also cause great harm to the human body. Western medicine therapy has unclear mechanism of action, poor efficacy of active ingredients in hair growth and hair blackening, and unsatisfactory therapeutic effect. Therefore, it is of great significance to find a drug that can effectively improve and treat leukotrichia and/or alopecia. However, no safe, rapid, and effective drug has been found so far. This application addresses the above issue.

Technical Solutions for Resolving the Technical Problem

The inventors unexpectedly discovered during the application research of sulforaphene that the sulforaphene has hair growth and hair blackening effects. In order to confirm the effect in this aspect, the inventors have conducted in-depth research, prepared a composition containing sulforaphene into granules, oral tablets, soft capsules and other dosage forms, and administered them to subjects. The results have showed that an appropriate dosage of the sulforaphene can effectively improve and treat leukotrichia and/or alopecia in a shorter time than the prior art.

The inventors have not found a mechanism of action of the sulforaphene in improving and treating the leukotrichia and/or alopecia, and will conduct research on this aspect in the future. According to current analysis, this mechanism may be related to an antioxidant function of the sulforaphene. This function improves the immunity of subjects with leukotrichia and alopecia, thereby preventing the leukotrichia or alopecia caused by excessive or abnormal responses of the immune system. The inventors also believe that sulforaphene may also promote the expression of MITF and prevent MITF from mutating. In this way, the accelerated abnormal coloring or differentiation of melanin differentiation cells caused by MITF mutations is prevented, thereby preventing the physiological aging of melanin stem cells. For the alopecia caused by dihydrotestosterone (DHT), sulforaphene may also prevent the conversion of testosterone into the DHT by inhibiting an activity of 5α-reductase. This process in turn prevents the DHT from combining with specific receptors to produce a protein that causes alopecia, thereby inhibiting the alopecia.

The present disclosure mainly relates to the following aspects:

1). The present disclosure provides a method of using a pharmaceutical composition for improving and treating leukotrichia and/or alopecia, including using ulforaphene where the sulforaphene serves as an active ingredient of the pharmaceutical composition, and the sulforaphene has a content of 0.1% to 50% based on a total weight of the pharmaceutical composition.

2). According to the method in 1), the sulforaphene has a content of 0.5% to 10%, more preferably 1% to 5%.

3). According to the method in 1) or 2), the sulforaphene is selected from the group consisting of a natural product extract, a biological synthesis product, and a chemical synthesis product.

4). According to the method in any one of 1) to 3), the natural product extract is derived from one selected from the group consisting of *Brassica oleracea* var. gemmifera *Zenker, Brassica oleracea* var. botrytis *Linnaeus, Brassica rapa* var. glabra *Regel*, kale, *Brassica oleracea* var. acephala DC., broccoli sprouts, *Brassica oleracea* var. albiflora *Kuntze*, cauliflower, *Brassica juncea* var. napiformis *Pailleux* et Bois, mustard, *Brassica rapa* L., *Raphanus sativus* L., *Eruca vesicaria* subsp. *sativa* (Miller) Thellung, and *Nasturtium officinale* R. Br. ex W. T. Aiton.

5). According to the method in any one of 1) to 4), the pharmaceutical composition is in the form of a tablet, a capsule, a pulvis, a powder, a water-soluble granule, a granule, an ointment, a patch, an emulsion, a liniment, a paste, an injection, a spray, a cream, a lotion, an oil, a suspension, a gel, or a tonic.

6). According to the method in any one of 1) to 5), the pharmaceutical composition is administered by oral administration, injection, skin administration, or mucosal administration.

7). According to the method in any one of 1) to 6), the pharmaceutical composition is subjected to oral administration at a dosage of 5 mg/person/day to 500 mg/person/day of the sulforaphene.

8). According to the method in 7), the pharmaceutical composition is subjected to oral administration at a dosage of 10 mg/person/day to 100 mg/person/day, more preferably 20 mg/person/day to 40 mg/person/day of the sulforaphene.

9). The present disclosure further provides a preparation method of a pharmaceutical composition including sulforaphene for improving and treating leukotrichia and/or alopecia, including: encapsulating the sulforaphene as an active ingredient into the pharmaceutical composition, where the sulforaphene has a content of 0.10% to 50% based on a total weight of the pharmaceutical composition.

Beneficial Effects of the Present Disclosure

In the present disclosure, the pharmaceutical composition containing sulforaphene as an active ingredient exhibits an extremely significant or even surprising effect in improving and treating leukotrichia and/or alopecia. The pharmaceutical composition can significantly promote the growth, repair, and increase of hair, surprisingly quickly reduce the degree of alopecia, and prevent the progression of alopecia. Meanwhile, the sulforaphene can promote the blackening of gray and white hair from the roots, harden the hair, and effectively repair and improve the hair quality. In addition, compared with the existing technology, the sulforaphene has a short action time and a significant medicinal effect, and is suitable for a wide range of people.

The beneficial effects of the present disclosure include:

(1) After subjects take the sulforaphene at a dosage of (10-100) mg/person/day orally, an improvement effect of leukotrichia and/or alopecia appears on 5 d to 15 d; after 20 d to 1 month, the white hair turns black, and new hair is obviously grown; after 2 to 3 months, most of the white hair turns black, the alopecia is significantly suppressed, and some subjects even grow new hair. In contrast, it takes at least 3 to 6 months for drugs in the prior art to have the effects of white hair blackening and/or alopecia being suppressed.

(2) For subjects with an area of leukotrichia and alopecia accounting for 1% to 10% of a total head area: after 1 month of administration, at least 94.0% of the subjects have obvious hair growth effect; at least 92.6% of the subjects had obvious hair blackening effect. For subjects with an area of leukotrichia and alopecia accounting for 10% to 50% of a total head area: after 2 months of administration, at least 92.8% of the subjects have obvious hair growth effect; at least 93.8% of the subjects had obvious hair blackening effect. For subjects with an area of leukotrichia and alopecia accounting for more than 50% of a total head area: after 3 months of administration, at least 86.8% of the subjects have obvious hair growth effect; at least 89.5% of the subjects had obvious hair blackening effect. Therefore, the pharmaceutical composition of the present disclosure is suitable for a wide range of subjects, has effects on most of the subjects, and is suitable for leukotrichia and/or alopecia caused by different reasons. However, no composition has been found in the prior art that can significantly improve and treat leukotrichia and/or alopecia for such a high proportion of people within a short period of 1 to 3 months.

Figure 2:
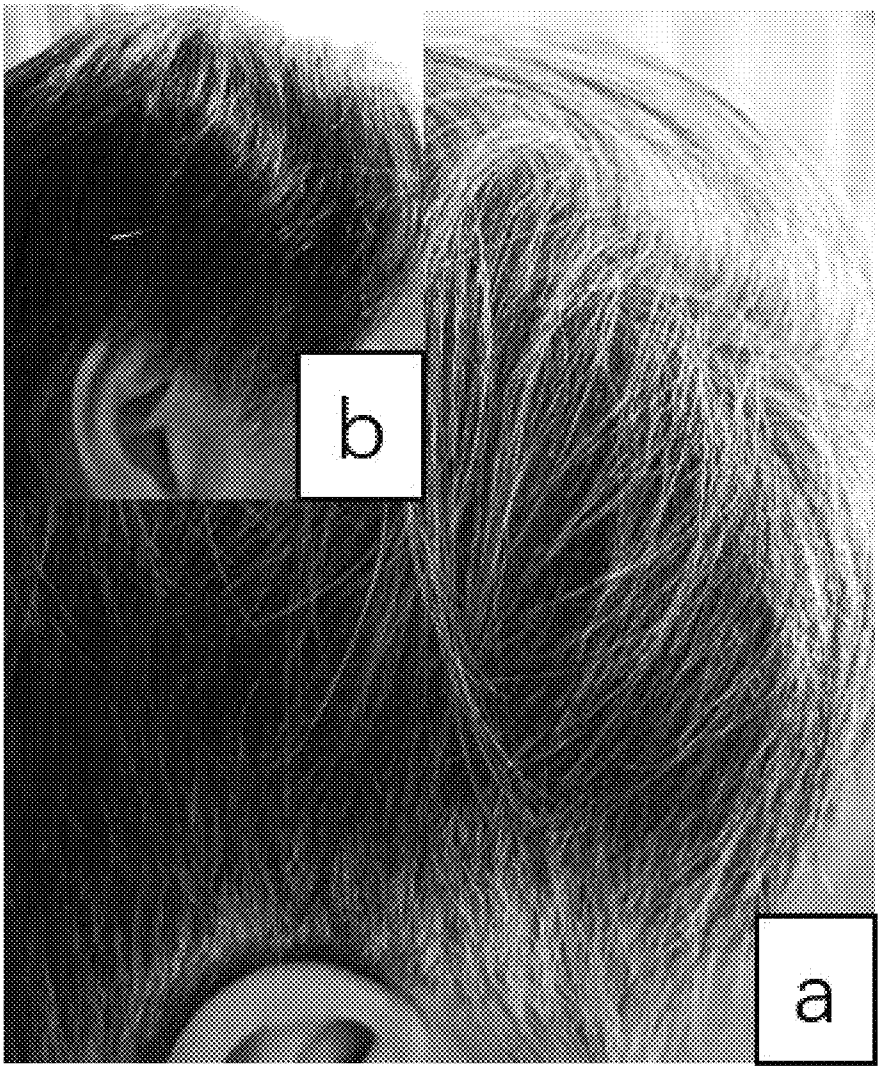

BRIEF DESCRIPTION OF THE DRAWINGS a and b in FIG. 1 show a comparison of hair photography of subjects with alopecia and leukotrichia after taking sulforaphene for 1 month and before taking same, respectively; and a and b in FIG. 2 show a comparison of hair photography of subjects with leukotrichia after taking sulforaphene for 2.5 month and before taking same, respectively.

DETAILED DESCRIPTION OF THE EMBODIMENTS

In the present disclosure, the pharmaceutical composition in which the sulforaphene is used as an active ingredient can improve and treat leukotrichia and/or alopecia, and is applicable to congenital and acquired leukotrichia, physiological and pathological leukotrichia, and physiological and pathological alopecia mentioned in the background.

In the present disclosure, there is no limitation on a content of the sulforaphene contained in the pharmaceutical composition, as long as the sulforaphene can achieve the effect of improving and treating leukotrichia and/or alopecia. The pharmaceutical composition may contain 0.1% to 50% by weight of sulforaphene. When the content of sulforaphene is less than 0.1% by weight, too low sulforaphene content may have no obvious effect on improving and treating leukotrichia and/or alopecia. When the content of sulforaphene is higher than 50% by weight, there is too much sulforaphene that cannot be well dissolved in the solvent and it is difficult to form a homogeneous phase.

In the present disclosure, the pharmaceutical composition includes preferably 0.5% to 10% by weight of sulforaphene. Within this range, the sulforaphene can significantly improve and treat leukotrichia and/or alopecia within a relatively short period of time, such as 2 to 3 months. The pharmaceutical composition includes more preferably 1% to 5% by weight of sulforaphene. Within this range, the sulforaphene can achieve a greater improvement and treatment of leukotrichia and/or alopecia in a short period of time. For example, for subjects with leukotrichia or alopecia accounting for more than 50% of the total head area, at least 86.8% and 89.5% of subjects have obvious hair growth and hair blackening effects within 3 months, respectively.

In the present disclosure, the sulforaphene can be prepared by any method known in the art, such as natural product extraction, biological synthesis, or chemical synthesis, as long as the sulforaphene extract has the effect of improving and treating leukotrichia and/or alopecia. In the present disclosure, the sulforaphene is preferably extracted from a natural product extract, and the natural product extract is derived from one selected from the group consisting of *Brassica oleracea* var. gemmifera *Zenker, Brassica oleracea* var. *botrytis Linnaeus, Brassica rapa* var. *glabra* Regel, kale, *Brassica oleracea* var. acephala DC., broccoli sprouts, *Brassica oleracea* var. albiflora *Kuntze*, cauliflower, *Brassica juncea* var. napiformis *Pailleux* et Bois, mustard, *Brassica rapa* L., *Raphanus sativus* L., *Eruca vesicaria* subsp. sativa (Miller) Thellung, and *Nasturtium officinale* R. Br. ex W. T. Aiton.

In a specific example of the present disclosure, a preparation method of the sulforaphene includes the following steps:

(1) crushing or homogenizing radish seeds or radish seed sprouts, adding 5 to 20 times a volume of tap water, deionized water, or a buffer solution with a pH value of 5.0 to 8.0, stirring at 5° C. to 50° C. to allow hydrolysis 10 min to 300 min, adding hydrochloric acid to adjust a pH value of a resulting hydrolyzate to 1.0 to 3.0, allowing to stand overnight, and conducting vacuum filtration or centrifugation to obtain a sulforaphene hydrolyzate;

(2) extracting the sulforaphene hydrolyzate obtained in step (1) 2 to 5 times with an organic solvent that is added in an amount 0.5 to 5 times a volume of the sulforaphene hydrolyzate, recovering the sulforaphene in the hydrolyzate, collecting an extraction layer in the organic solvent, distilling the extraction layer under reduced pressure to obtain a crude extract of the sulforaphene, while recovering the organic solvent; where the organic solvent is an organic solvent commonly used in this field, such as n-hexane, cyclohexane, diethyl ether, n-butanol, chloroform, dichloromethane, or ethyl acetate;

(3) adding the crude extract of sulforaphene obtained in step (2) to a molecular distillation device to allow first-stage molecular distillation to remove residual organic solvents, moisture, and low-boiling point impurities in the crude extract of sulforaphene, collecting a heavy component flowing out from a distillation wall of a first-stage molecular distillation device to obtain a first-stage molecular distillation heavy component; where the conditions for the first-stage molecular distillation include: raw material insulation temperature of 30° C. to 60° C., vacuum degree of 100 Pa to 2,000 Pa, distillation temperature of 50° C. to 100° C., feeding flow rate of 2 mL/min to 20 mL/min, condensation surface temperature of 0° C. to 30° C., and film scraper speed of 200 rpm to 400 rpm; and (4) adding the first-stage molecular distillation heavy component obtained in step (3) into the molecular distillation device to allow second-stage molecular distillation to remove high-boiling point impurities in the first-stage molecular distillation heavy component, collecting a light component flowing out from a condensation surface of a second-stage molecular distillation device to obtain the sulforaphene; where the conditions for the second-stage molecular distillation include: raw material insulation temperature of 30° C. to 70° C., vacuum degree of 0.1 Pa to 10 Pa, distillation temperature of 80° C. to 200° C., feeding flow rate of 1 mL/min to 10 mL/min, condensation surface temperature of 0° C. to 20° C., and film scraper speed of 200 rpm to 450 rpm.

In the present disclosure, the pharmaceutical composition can be made into an appropriate dosage form according to a shape of the product. For example, the pharmaceutical composition is in the form of a tablet, a capsule, a pulvis, a powder, a water-soluble granule, a granule, an ointment, a patch, an emulsion, a liniment, a paste, an injection, a spray, a cream, a lotion, an oil, a suspension, a gel, or a tonic, but is not limited to the above selections.

In the present disclosure, the pharmaceutical composition may be a daily chemical such as health care products, food, or hair care products. As long as the effect of improving and treating leukotrichia and/or alopecia can be achieved, a use form of the pharmaceutical composition is not limited thereto.

In the present disclosure, the pharmaceutical composition may include any pharmaceutically acceptable carrier and/or excipient known in the art, as long as it does not affect the effect of the present disclosure achieved by the sulforaphene. For example, lactose, glucose, sucrose, sorbitol, mannitol, starch, dextrin, acacia, calcium phosphate, alginate, gelatin, calcium silicate, microcrystalline cellulose, polyvinylpyrrolidone, water, syrup, methylcellulose, methylparaben, propylparaben, talc, magnesium stearate, super sodium starch glycolate, vegetable oil, animal oil, and mineral oil, but the present disclosure is not limited thereto.

In the present disclosure, in addition to the above ingredients, the pharmaceutical composition may also include other additives, such as lubricants, wetting agents, sweeteners, flavors, emulsifiers, suspending agents, and preservatives. As long as it does not affect the effect of the present disclosure achieved by the sulforaphene, any additive can be added.

In the present disclosure, the pharmaceutical composition can be administered by oral administration, injection, skin administration, or mucosal administration. As long as the effect of improving and treating leukotrichia and/or alopecia can be achieved, the administration form of the pharmaceutical composition is not limited thereto.

In the present disclosure, the dosage, administration frequency, and administration time of the pharmaceutical composition may vary according to the subject's leukotrichia or alopecia symptoms, the subject's age, and the pharmaceutical dosage form. The sulforaphene in the pharmaceutical composition is preferably taken orally at a dose of (5-500) mg/person/day, more preferably (10-100) mg/person/day, and most preferably (20-40) mg/person/day. Taking granules, oral preparations, and soft capsules as examples, generally the administration frequency is (1-2) times/day, the dosage is (10-100) mg/person/day, and the administration time is 5 d to 3 months.

The present disclosure is further described below with reference to specific examples, but the protection scope the present disclosure is not limited thereto.

EXAMPLE

Preparation of Sulforaphene Extract

The sulforaphene extract was prepared according to the following steps for use in the compositions of the examples described later.

(1) 100 kg of radish seeds or radish seed sprouts were crushed or homogenized, 2,000 L of 20 times a volume of deionized water was added, stirred at room temperature to allow hydrolysis 5 h, hydrochloric acid was added to adjust a pH value of a resulting hydrolyzate to 2.0, allowed to stand overnight, and centrifugation was conducted to obtain 2,000 L of a sulforaphene hydrolyzate as a supernatant;

(2) the sulforaphene hydrolyzate obtained in step (1) was extracted 3 times with an same volume of ethyl acetate, the sulforaphene in the hydrolyzate was recovered, an extraction layer in the ethyl acetate was collected, the extraction layer was distilled under reduced pressure at 40° C. and a vacuum degree of −0.08 MPa to obtain 200 L of a crude extract of the sulforaphene, while the ethyl acetate was recovered;

(3) the crude extract of sulforaphene obtained in step (2) was added to a molecular distillation device to allow first-stage molecular distillation to remove residual ethyl acetate, moisture, and low-boiling point impurities in the crude extract of sulforaphene, a heavy component flowing out from a distillation wall of a first-stage molecular distillation device was collected to obtain 2,000 g of a first-stage molecular distillation heavy component; where the conditions for the first-stage molecular distillation included: raw material insulation temperature of 60° C., vacuum degree of 2,000 Pa, distillation temperature of 100° C., feeding flow rate of 2 mL/min, condensation surface temperature of 0° C., and film scraper speed of 400 rpm; and (4) the first-stage molecular distillation heavy component obtained in step (3) was added into the molecular distillation device to allow second-stage molecular distillation to remove high-boiling point impurities in the first-stage molecular distillation heavy component, a light component flowing out from a condensation surface of a second-stage molecular distillation device was collected to obtain 1,000 g of the sulforaphene with a high purity of 99.5%; where the conditions for the second-stage molecular distillation included: raw material insulation temperature of 70° C., vacuum degree of 0.1 Pa, distillation temperature of 110° C., feeding flow rate of 1 mL/min, condensation surface temperature of 0° C., and film scraper speed of 450 rpm.

<Preparation of the Pharmaceutical Composition of the Present Disclosure Containing Sulforaphene as an Active Ingredient>

The pharmaceutical composition of the present disclosure was prepared in the form of granules, tablets, and capsules by mixing the sulforaphene extract prepared by the above method as a raw material with other additives.

Example 1 Preparation of Sulforaphene Water-Soluble Granule 1

100 g of the sulforaphene extract prepared by the above method and 19.9 kg of dextrin were mixed and dissolved in 100 L of deionized water, and then spray-dried. The spray drying was conducted at an air inlet temperature of 180° C., an air outlet temperature of 80° C., and a liquid inlet speed of 5 L/h. A product was collected to prepare a spray-dried powder of sulforaphene to allow granulation in a granulator, and obtained granules were sub-packed in 2 g by an automatic granule packaging machine to prepare the sulforaphene water-soluble granule 1 with a 0.5% sulforaphene content.

Example 2 Preparation of Sulforaphene Water-Soluble Granule 2

100 g of the sulforaphene extract prepared by the above method and 9.9 kg of dextrin were mixed and dissolved in 50 L of deionized water, and then spray-dried in a same manner as that in Example 1 to prepare a spray-dried powder of sulforaphene. The powder was sub-packed in 1 g to prepare the sulforaphene water-soluble granule 2 with a 1% sulforaphene content.

Example 3 Preparation of Sulforaphene Water-Soluble Granule 3

100 g of the sulforaphene extract prepared by the above method and 99.9 kg of dextrin were mixed and dissolved in 500 L of deionized water, and then spray-dried in a same manner as that in Example 1 to prepare a spray-dried powder of sulforaphene. The powder was sub-packed in 20 g to prepare the sulforaphene water-soluble granule 3 with a 0.1% sulforaphene content.

Example 4 Preparation of Sulforaphene Oral Tablet 1

100 g of the sulforaphene extract prepared by the above method and 1.9 kg of dextrin were mixed and dissolved in 10 L of deionized water, and then spray-dried in a same manner as that in Example 1 to prepare a spray-dried powder of sulforaphene with a 5% sulforaphene content. 50 g of magnesium stearate, 500 g of Peng Su Wang (super carboxymethyl starch sodium), and 2.45 kg of microcrystalline cellulose were added to the dried powder, mixed well to allow dry granulation, and then obtained drug-containing granules were tableted to obtain the oral tablet 1 containing 2% sulforaphene with a specification of 500 mg per tablet.

Example 5 Preparation of Sulforaphene Oral Tablet 2

200 g of the sulforaphene extract prepared by the above method and 1.8 kg of dextrin were mixed and dissolved in 10 L of deionized water, and then spray-dried in a same manner as that in Example 1 to prepare a spray-dried powder of sulforaphene with a 10% sulforaphene content. 50 g of magnesium stearate, 500 g of Peng Su Wang, and 2.45 kg of microcrystalline cellulose were added and mixed well to allow tableting to obtain the oral tablet 2 containing 4% sulforaphene with a specification of 500 mg per tablet.

Example 6 Preparation of Sulforaphene Oral Tablet 3

100 g of the sulforaphene extract prepared by the above method and 0.9 kg of dextrin were mixed and dissolved in 5 L of deionized water, and then spray-dried in a same manner as that in Example 1 to prepare a spray-dried powder of sulforaphene with a 10% sulforaphene content. 100 g of magnesium stearate, 1 kg of Peng Su Wang, and 7.9 kg of microcrystalline cellulose were added and mixed well to allow tableting to obtain the oral tablet 3 containing 1% sulforaphene with a specification of 500 mg per tablet.

Example 7 Preparation of Sulforaphene Soft Capsule 1

100 g of the sulforaphene extract prepared by the above method were mixed with 4.9 kg of corn oil, gelatin was used as a main component of a capsule skin, and the sulforaphene soft capsule 1 with a content of 2% were prepared by mold pressing according to methods known in the art, where each soft capsule included 500 mg of contents.

Example 8 Preparation of Sulforaphene Soft Capsule 2

100 g of the sulforaphene extract prepared by the above method were mixed with 4.9 kg of soybean oil, and the sulforaphene soft capsule 2 with a content of 2% were prepared by a same method as that in Example 7, where each soft capsule included 250 mg of contents.

Example 9 Preparation of Sulforaphene Soft Capsule 3

100 g of the sulforaphene extract prepared by the above method were mixed with 9.9 kg of soybean oil, and the sulforaphene soft capsule 3 with a content of 1% were prepared by a same method as that in Example 7, where each soft capsule included 500 mg of contents.

<Improvement and Treatment of Leukotrichia and/or Alopecia by the Pharmaceutical Composition of the Present Disclosure>

The following experiments were conducted using the sulforaphene granules, tablets, and soft capsules prepared in Examples 1 to 9 to investigate the improvement and therapeutic effect of sulforaphene on leukotrichia and/or alopecia.

Through voluntary participation, 347 subjects aged 18 to 65 years old, with different causes and symptoms of leukotrichia and/or alopecia, and regardless of gender, were selected. The subjects took the sulforaphene granules, tablets, or soft capsules prepared in Examples 1 to 9, 1 to 2 times a day, 1 to 6 capsules at each time, after meals by oral administration at a dosage of (10-100) mg/person/day for 1 to 3 months. The dosage was determined by the following factors: the subject's weight, age, severity of leukotrichia and/or alopecia, and acceptance of the drug.

The experimental results were shown in Tables 1 to 2 below. FIG. 1 to FIG. 2 were hair photography pictures, showing the improvement and therapeutic effect of leukotrichia and/or alopecia after the subjects took sulforaphene.

It should be noted that in Tables 1a and 1b, "improvement start time" meant the time when white hair turned black and/or alopecia reduction effect began to appear, and women mainly show whether alopecia occurred when combing hair; "Whether other drugs were used" meant whether the subject had ever taken other drugs to improve or treat leukotrichia and/or alopecia. In Table 2, the "use time" was set according to the degree of leukotrichia and/or alopecia of the subjects. For subjects whose leukotrichia and/or alopecia proportion accounted for 1% to 10% of the whole head, the use time was set to continuous intake of sulforaphene for 1 month; for subjects whose leukotrichia and/or alopecia proportion accounted for 10% to 50% of the whole head, the use time was set to continuous intake of sulforaphene for 2 months; for subjects whose leukotrichia and/or alopecia proportion accounted for more than 50% of the whole head, the use time was set to continuous intake of sulforaphene for 3 months. In Table 2, "Obvious" meant that hair growth and hair blackening increased significantly, and the area of hair growth or hair blackening was greater than 25% of the total hair area; "Normal" meant that hair growth and hair blackening had increased, and the area of hair growth or hair blackening was 1% to 25% of the total hair area; "Ineffective" meant that there was no obvious effect, and the area of hair growth or hair blackening was less than 1% of the total hair area.

TABLE 1a

Improvement and therapeutic effect of male taking sulforaphene on leukotrichia and/or alopecia

| | No. | | | | |
|---|---|---|---|---|---|
| | 1 | 2 | 3 | 4 | 5 |
| Gender | Male | Male | Male | Male | Male |
| Age | 35 | 42 | 48 | 55 | 18 |
| Incidence Age | 30 | 40 | 40 | 45 | 16 |
| Alopecia Range | Head top | Forehead | None | None | None |
| Family history of baldness | None | None | None | None | None |
| White hair range | None | None | Whole head, about ½ of white hair | Whole head, basically fully white | Head top, about ⅓ of white hair |
| Family history of leukotrichia | None | None | None | None | Yes |
| Dosage and dosage form of sulforaphene | 10 mg/d Water-soluble granule | 30 mg/d Water-soluble granule | 30 mg/d Tablet | 60 mg/d Tablet | 30 mg/d Soft capsule |
| Improvement start time | Alopecia decreased and new hair appeared after 15 d | New hair appeared after 10 d | New hair appeared after 20 d | New hair appeared after 15 d | New hair appeared after 10 d |
| Improvement effect | New hair was obvious at alopecia site after 1 month, and length of the new hair exceeded 1 cm after 2 months | Obvious new hair at hairline on forehead after 20 d | More than ½ of the white hair turned gray after 1 month, all white hair turned gray after 1.5 months, and all white hair basically turned black after 2 months | More than ½ of white hair turned gray after 1 month, and all white hair basically turned black after 2.5 months | All white hair basically turned black after 1 month |
| Whether other drugs were used | None | None | None | None | None |

TABLE 1b

Improvement and therapeutic effect of female taking sulforaphene on leukotrichia and/or alopecia

| | No. | | | | |
|---|---|---|---|---|---|
| | 1 | 2 | 3 | 4 | 5 |
| Gender | Female | Female | Female | Female | Female |
| Age | 35 | 65 | 48 | 42 | 32 |
| Incidence Age | 32 | 55 | 40 | 40 | 22 |
| Alopecia range | Whole head, less alopecia when combing hair | Whole head, more alopecia when combing hair | Whole head, more alopecia when combing hair | None | None |
| Family history of baldness | None | None | None | None | None |

TABLE 1b-continued

Improvement and therapeutic effect of female taking sulforaphene on leukotrichia and/or alopecia

| | No. 1 | 2 | 3 | 4 | 5 |
|---|---|---|---|---|---|
| White hair range | Whole head, about 1/10 of white hair | Whole head, about 1/3 of white hair | None | Whole head, about 1/10 of white hair | Whole head, about 1/2 of white hair |
| Family history of leukotrichia | None | None | None | None | Yes |
| Dosage and dosage form of sulforaphene | 30 mg/d Water-soluble granule | 10 mg/d Water-soluble granule | 30 mg/d Tablet | 10 mg/d Tablet | 30 mg/d Soft capsule |
| Improvement start time | Reduced alopecia appeared after 5 d | Reduced alopecia appeared after 10 d | Reduced alopecia appeared after 5 d | White hair blackening appeared after 10 d | White hair blackening appeared after 15 d |
| Improvement effect | Alopecia was significantly reduced when combing hair after 10 d, and there was basically no alopecia after 1 month and most of white hair turned black | Alopecia had improved significantly and some white hair turned gray after 1 month, and all white hair basically turned black after 2 months | Basically no alopecia after 1 month | Roots of white hair turned gray after 20 d, and all white hair basically turned black after two months | More than 1/2 of white hair turned gray after 1 month, all white hair turned gray after 1.5 months, and all white hair basically turned black after 2.5 months |
| Whether other drugs were used | Using traditional Chinese medicine for hair growth 2 years ago, and there was no improvement for half a year | None | None | None | None |

TABLE 2

Proportion of subjects with improvement and treatment effect on leukotrichia and/or alopecia

| Use time | Number of subjects | Hair growth effect Obvious | Normal | Ineffective | Hair blackening effect Obvious | Normal | Ineffective |
|---|---|---|---|---|---|---|---|
| One month | 50 | 47 | 2 | 1 | 48 | 2 | 0 |
| | Male | 94.0% | 4.0% | 2.0% | 96.0% | 4.0% | 0.0% |
| | 54 | 51 | 2 | 1 | 50 | 3 | 1 |
| | Female | 94.4% | 3.7% | 1.9% | 92.6% | 5.6% | 1.9% |
| Two months | 81 | 77 | 1 | 3 | 76 | 3 | 2 |
| | Male | 95.1% | 1.2% | 3.7% | 93.8% | 3.7% | 2.5% |
| | 69 | 64 | 3 | 2 | 65 | 4 | 0 |
| | Female | 92.8% | 4.3% | 2.9% | 94.2% | 5.8% | 0.0% |
| 3 months | 38 | 33 | 5 | 0 | 34 | 4 | 0 |
| | Male | 86.8% | 13.2% | 0.0% | 89.5% | 10.5% | 0.0% |
| | 55 | 51 | 2 | 2 | 54 | 0 | 1 |
| | Female | 92.7% | 3.6% | 3.6% | 98.2% | 0.0% | 1.8% |

Table 1a and Table 1b showed that or subjects of different ages and genders, suffering from different degrees of leukotrichia and/or alopecia, after oral administration at a dose of (10-60) mg/person/day, there were varying degrees of improvement between 5 d and 3 months. As shown in No. 1 in Table 1b, this subject suffered from both leukotrichia and alopecia, and improvement effects occurred Within a short period of time after taking sulforaphene. That is, after oral administration of sulforaphene water-soluble granules at a dose of 30 mg/day, alopecia began to decrease after 5 d, and after one month there was basically no alopecia and most of the white hair turned black. This subject had been treated with other traditional Chinese medicines 2 years ago, but the leukotrichia and alopecia did not improve after half a year of continuous treatment. For subjects with severe leukotrichia, such as the subject of No. 4 in Table 1a, whose hair was basically completely white, more than 1/2 of the white hair turned gray after T month, and all white hair turned basically black after 2.5 months (a and b in FIG. 2).

In addition, a and b in FIG. T also showed the subjects of No. 2 suffered from both alopecia and leukotrichia in Table 1b; after taking sulforaphene for T month, the alopecia was improved significantly, some white hair turned gray, and the white hair basically turned black after 2 months. The hair photography confirmed that the white hair turned black, and the blackened hair was hard and shiny, showing the hair blackening and hair nourishing effects of sulforaphene.

Table 2 showed the improvement and degree of treatment within a specific time period of the study when being administered for 1 month, 2 months, and 3 months separately according to the severity of leukotrichia and alopecia. The results showed that: after taking sulforaphene for 1 month, at least 94.0% of subjects with leukotrichia or alopecia accounting for 1 to 10% of their head had obvious hair growth effect, and at least 92.6% of the subjects had obvious hair blackening effect. This indicated that for subjects with mild leukotrichia and alopecia, the sulforaphene showed an extremely significantly therapeutic effect. For subjects with moderate leukotrichia or alopecia, such as subjects with leukotrichia or alopecia accounting for 10% to 50% of their whole head: after taking sulforaphene for 2 months, at least 92.8% of subjects had obvious hair growth effect, and at least 93.8% of the subjects had obvious hair blackening effect. Even for subjects with severe symptoms of leukotrichia or alopecia ratio of more than 50% of their whole head: after taking sulforaphene for 3 months, at least 86.8% of subjects had obvious hair growth effect, and at least 89.5% of the subjects had obvious hair blackening effect.

The experiments also showed that compositions containing sulforaphene in different dosage forms such as granules, oral dosage forms, and soft capsules could improve and treat leukotrichia and/or alopecia in subjects. The experiment did not find any significant difference in the improvement and therapeutic effect of the dosage forms.

INDUSTRIAL APPLICABILITY

In the present disclosure, the pharmaceutical composition containing sulforaphene as an active ingredient had a highly significant effect in improving and treating leukotrichia and/or alopecia. The pharmaceutical composition shows short drug action time, significant drug effect, and wide adaptability to a wide range of people. After the subject takes the pharmaceutical composition of the present disclosure, the improvement effect of leukotrichia and/or alopecia begins to appear in 5 d to 15 d; after 2 to 3 months, most of the white hair turned black, and the alopecia inhibition effect was remarkable; some subjects even had new hair grown. Therefore, the present disclosure provides a new drug and method for the current improvement and treatment of leukotrichia and/or alopecia.

What is claimed is:

1. A method of improving and treating leukotrichia and/or alopecia, comprising administering to a subject in need thereof a pharmaceutical composition comprising sulforaphene at a dosage of 5 mg/person/day to 500 mg/person/day, wherein the sulforaphene serves as an active ingredient of the pharmaceutical composition, and the sulforaphene has a content of 0.1% to 50% based on a total weight of the pharmaceutical composition.

2. The method according to claim 1, wherein the sulforaphene has a content of 0.5% to 10%.

3. The method according to claim 1, wherein the sulforaphene is selected from the group consisting of a natural product extract, a biological synthesis product, and a chemical synthesis product.

4. The method according to claim 2, wherein the sulforaphene is selected from the group consisting of a natural product extract, a biological synthesis product, and a chemical synthesis product.

5. The method according to claim 1, wherein the natural product extract is derived from one selected from the group consisting of *Brassica oleracea* var. gemmifera *Zenker, Brassica oleracea* var. *botrytis Linnaeus, Brassica rapa* var. glabra *Regel*, kale, *Brassica oleracea* var. acephala DC, broccoli sprouts, *Brassica oleracea* var. albiflora *Kuntze*, cauliflower, *Brassica juncea* var. napiformis *Pailleux* et Bois, mustard, *Brassica rapa* L., *Raphanus sativus* L., *Eruca vesicaria* subsp. sativa (Miller) Thellung, and *Nasturtium officinale* R. Br. ex W. T. Aiton.

6. The method according to claim 2, wherein the natural product extract is derived from one selected from the group consisting of *Brassica oleracea* var. gemmifera *Zenker, Brassica oleracea* var. *botrytis Linnaeus, Brassica rapa* var. glabra *Regel*, kale, *Brassica oleracea* var. acephala DC, broccoli sprouts, *Brassica oleracea* var. albiflora *Kuntze*, cauliflower, *Brassica juncea* var. napiformis *Pailleux* et Bois, mustard, *Brassica rapa* L., *Raphanus sativus* L., *Eruca vesicaria* subsp. *sativa* (Miller) Thellung, and *Nasturtium officinale* R. Br. ex W. T. Aiton.

7. The method according to claim 3, wherein the natural product extract is derived from one selected from the group consisting of *Brassica oleracea* var. gemmifera *Zenker, Brassica oleracea* var. *botrytis Linnaeus, Brassica rapa* var. glabra *Regel*, kale, *Brassica oleracea* var. acephala DC, broccoli sprouts, *Brassica oleracea* var. albiflora *Kuntze*, cauliflower, *Brassica juncea* var. napiformis *Pailleux* et Bois, mustard, *Brassica rapa* L., *Raphanus sativus* L., *Eruca vesicaria* subsp. sativa (Miller) Thellung, and *Nasturtium officinale* R. Br. ex W. T. Aiton.

8. The method according to claim 4, wherein the natural product extract is derived from one selected from the group consisting of *Brassica oleracea* var. gemmifera *Zenker, Brassica oleracea* var. *botrytis Linnaeus, Brassica rapa* var. glabra *Regel*, kale, *Brassica oleracea* var. acephala DC, broccoli sprouts, *Brassica oleracea* var. albiflora *Kuntze*, cauliflower, *Brassica juncea* var. napiformis *Pailleux* et Bois, mustard, *Brassica rapa* L., *Raphanus sativus* L., *Eruca vesicaria* subsp. *sativa* (Miller) Thellung, and *Nasturtium officinale* R. Br. ex W. T. Aiton.

9. The method according to claim 1, wherein the pharmaceutical composition is in the form of a tablet, a capsule, a pulvis, a powder, a water-soluble granule, a granule, an ointment, a patch, an emulsion, a liniment, a paste, an injection, a spray, a cream, a lotion, an oil, a suspension, a gel, or a tonic.

10. The method according to claim 2, wherein the pharmaceutical composition is in the form of a tablet, a capsule, a pulvis, a powder, a water-soluble granule, a granule, an ointment, a patch, an emulsion, a liniment, a paste, an injection, a spray, a cream, a lotion, an oil, a suspension, a gel, or a tonic.

11. The method according to claim 3, wherein the pharmaceutical composition is in the form of a tablet, a capsule, a pulvis, a powder, a water-soluble granule, a granule, an ointment, a patch, an emulsion, a liniment, a paste, an injection, a spray, a cream, a lotion, an oil, a suspension, a gel, or a tonic.

12. The method according to claim 4, wherein the pharmaceutical composition is in the form of a tablet, a capsule, a pulvis, a powder, a water-soluble granule, a granule, an ointment, a patch, an emulsion, a liniment, a paste, an injection, a spray, a cream, a lotion, an oil, a suspension, a gel, or a tonic.

13. The method according to claim 5, wherein the pharmaceutical composition is in the form of a tablet, a capsule, a pulvis, a powder, a water-soluble granule, a granule, an ointment, a patch, an emulsion, a liniment, a paste, an injection, a spray, a cream, a lotion, an oil, a suspension, a gel, or a tonic.

14. The method according to claim 6, wherein the pharmaceutical composition is in the form of a tablet, a capsule, a pulvis, a powder, a water-soluble granule, a granule, an ointment, a patch, an emulsion, a liniment, a paste, an injection, a spray, a cream, a lotion, an oil, a suspension, a gel, or a tonic.

15. The method according to claim 7, wherein the pharmaceutical composition is in the form of a tablet, a capsule, a pulvis, a powder, a water-soluble granule, a granule, an ointment, a patch, an emulsion, a liniment, a paste, an injection, a spray, a cream, a lotion, an oil, a suspension, a gel, or a tonic.

16. The method according to claim 8, wherein the pharmaceutical composition is in the form of a tablet, a capsule, a pulvis, a powder, a water-soluble granule, a granule, an ointment, a patch, an emulsion, a liniment, a paste, an injection, a spray, a cream, a lotion, an oil, a suspension, a gel, or a tonic.

17. The method according to claim 1, wherein the pharmaceutical composition is administered by oral administration, injection, skin administration, or mucosal administration.

18. The method according to claim 1, wherein the pharmaceutical composition is subjected to oral administration at a dosage of 10 mg/person/day to 100 mg/person/day.

19. The method according to claim 1, wherein the sulforaphene has a content of 1% to 5%.

* * * * *